United States Patent [19]
Beebe et al.

[11] Patent Number: 5,472,881
[45] Date of Patent: Dec. 5, 1995

[54] THIOL LABELING OF DNA FOR ATTACHMENT TO GOLD SURFACES

[75] Inventors: Thomas P. Beebe, Salt Lake City, Utah; Carol E. Rabke-Clemmer, Rochester, N.Y.

[73] Assignee: University of Utah Research Foundation, Salt Lake City, Utah

[21] Appl. No.: 215,136

[22] Filed: Mar. 21, 1994

Related U.S. Application Data

[63] Continuation-in-part of Ser. No. 974,564, Nov. 12, 1992, abandoned.

[51] Int. Cl.$^6$ .............................. C12Q 1/68; G01N 33/00
[52] U.S. Cl. ................... 436/94; 436/501; 435/6; 935/77; 250/306; 250/307; 250/311
[58] Field of Search .............................. 436/94, 174, 178, 436/525, 501; 435/6, 91; 536/27.11; 250/306, 307, 311; 935/77

[56] References Cited

U.S. PATENT DOCUMENTS

| | | | |
|---|---|---|---|
| 4,868,396 | 9/1989 | Lindsay | 250/306 X |
| 4,920,059 | 4/1990 | Moeremans et al. | 435/6 X |
| 5,073,483 | 12/1991 | Lebacq | 435/6 |
| 5,106,729 | 4/1992 | Lindsay et al. | 435/6 |
| 5,151,510 | 9/1992 | Stec et al. | 435/6 X |
| 5,155,361 | 10/1992 | Lindsay | 250/307 |
| 5,294,369 | 3/1994 | Shigekawa et al. | 436/525 X |

OTHER PUBLICATIONS

Lindsay et al., Science, vol. 244, Jun. 2, 1989, pp. 1063–1064.
Bain et al., Journal American Chemical Society, vol. 111, 1989, pp. 321–335.
Bain et al., Journal American Chemical Society, vol. 111, 1989, pp. 7155–7164.

*Primary Examiner*—James C. Housel
*Assistant Examiner*—Maureen M. Wallenhorst
*Attorney, Agent, or Firm*—Thorpe, North & Western

[57] ABSTRACT

A method for adsorbing nucleic acids to a surface of a gold substrate for analyzing the structure of the nucleic acid includes the steps of thiolating the nucleic acid by substituting at least one non-bridging internucleotide oxygen of each phosphodiester moiety with sulfur, depositing the thiolated nucleic acid on the gold surface, and subjecting the nucleic acid to analysis for determining the atomic or molecular structure thereof. The gold surface is prepared by subjecting a gold single crystal to mechanical polishing, electropolishing, cleaning by cycles of $Ar^+$ sputtering and annealing under vacuum until no contamination is detected by Auger electron spectroscopy, and flame annealing and quenching in methanol. Gold films deposited on atomically flat substrates, such as mica, can also be used. The thiolated DNA is deposited on the gold surface for a sufficient time for covalent bonds to form between the sulfur and the gold. Scanning tunneling microscopy, atomic force microscopy, angle-dependent x-ray photoelectron spectroscopy, and Auger electron spectroscopy are used to analyze the nucleic acid structure.

19 Claims, 6 Drawing Sheets

THIOL LABELING OF DNA FOR ATTACHMENT TO GOLD SURFACES

This is a continuation-in-part of application Ser. No. 07/974,564, filed Nov. 12, 1992, and now abandoned.

BACKGROUND OF THE INVENTION

This invention relates to a method for attaching nucleic acids to surfaces to permit structural analysis of the nucleic acids. More particularly, this invention relates to a method for attaching DNA or RNA to a gold surface for structural analysis of the DNA or RNA by Auger electron spectroscopy, angle-dependent x-ray photoelectron spectroscopy, scanning tunneling microscopy, atomic force microscopy, and the like.

Structural analysis of nucleic acids suddenly became important in 1953 when Watson and Crick discovered that deoxyribonucleic acid (DNA) is the biological molecule that stores genetic information and transfers that information from generation to generation. In succeeding years, ribonucleic acids (RNAs) were also shown to play a role in genetics as messenger RNAs and transfer RNAs. Further, studies of viruses such as tobacco mosaic virus (TMV) demonstrated that RNA was capable of serving as a repository of genetic information.

Prior to 1977, structural analysis of DNA and RNA was difficult, expensive, and time-consuming. However, in that year two methods for determining the sequence of bases in DNA were discovered independently that made nucleotide sequencing of DNA easier, cheaper, and faster. These two methods are the chemical degradation method of Maxam and Gilbert, 74 Proc. Nat'l Acad. Sci. USA 560–64 (1977), and the chain termination method of Sanger, 74 Proc. Nat'l Acad. Sci. USA 5463–67 (1977). At about the same time, techniques of molecular cloning were developed so that DNA copies of RNA molecules could be cloned and sequenced by these two methods. Direct RNA sequencing techniques were also developed.

The chemical degradation method of DNA sequencing is based on the concept of partially degrading DNA fragments through four base-specific degradation reactions, one for each of the four bases. Degradation of a base makes the phosphodiester backbone more susceptible to chemical cleavage. Thus, after the bases are specifically degraded, the DNA fragments are subjected to another reaction to break the phosphodiester backbone. The specifically degraded fragments are then size fractionated. Labeling of the fragments with radioactive, fluorescent, chemiluminescent or other labels permits the fragments to be detected. Thus, a nucleotide can be identified and assigned to each position in the nucleotide chain by the reaction that specifically degraded the base at that position.

The chain termination method also relies on four different reactions to deduce the identity of each nucleotide in a chain. However, these reactions involve synthesis of nucleotide chains rather than their degradation. DNA is normally double-stranded and each base in a nucleotide chain is bonded to a complementary base in the other nucleotide chain. Guanine (G) pairs with cytosine (C) and adenine (A) pairs with thymine (T). Thus, if one knows the sequence of one strand of the DNA, the sequence of the other strand is also known. DNA polymerases are available which will synthesize a complementary strand of DNA if provided with a single-stranded DNA template and an oligo- or polynucleotide primer for providing a hydroxyl group to which the next nucleotide in the chain is attached. Addition of chain terminating nucleotide analogs, such as 2',3'-dideoxynucleoside triphosphates that lack the hydroxyl group to which the next nucleotide in the chain would ordinarily be attached, makes it possible to terminate a chain at every possible nucleotide position. By using four chain-terminating reactions, each one, respectively, containing a chain terminating analog of one of the four nucleotides in DNA, the sequence of nucleotides in the chain can be determined. The chains are labeled as in the chemical degradation technique with radioactive, fluorescent, chemiluminescent, or other labels. The chains are then fractionated by length. In this way the sequence of nucleotides in the chain can be deduced by identifying the nucleotide analog that terminates a chain at each position in the DNA.

Despite the huge improvement that these two techniques have been to determining the structure of DNA molecules at the nucleotide sequence level, significant additional improvements are still needed to increase the speed and reduce the cost of sequencing large nucleic acids. Without such improvements it will not be feasible to sequence the entire three billion basepairs of DNA that comprise the entire genetic complement of a human being in a timely and economical manner. Other large sequencing projects will, likewise, be impractical. Alternative methods of nucleotide sequencing to those just described are being developed.

A method that has been suggested for rapid sequencing of nucleic acids is through imaging of the nucleic acid with techniques such as scanning tunneling microscopy (STM) and atomic force microscopy (AFM). These recently developed methods utilize microscopes that make it possible to resolve or visualize individual atoms in some samples. In principle, it should be possible to attach nucleic acids to suitable substrates and visualize the nucleic acids by STM or AFM. The nucleotide sequence of a nucleic acid could be read by visually identifying each base from an image of the nucleic acid, or by detecting some other non-visual signal (spectroscopic) which is unique to the various bases. In practice, the potential for sequencing nucleic acids by STM or AFM imaging has suffered from several technical stumbling blocks. For example, suitable substrates are needed that are both atomically flat and free of contaminants or other artifacts that would interfere with producing readable images. A further problem has been that the nucleic acid must adhere to the substrate so that the nucleic acid does not move during the minutes that are needed to produce the image. Clearly, a moving target is not an ideal subject for a readable image. Thus, a method of attaching nucleic acids to an atomically flat, contaminant free substrate so that the nucleic acids are firmly anchored and do not move would be very important to structural analysis of nucleic acids using methods that distinguish the atomic or molecular structure of the nucleic acid. Further, a method is needed for binding the nucleic acid to the substrate so that the nucleic acid is oriented for imaging of the bases. Binding the phosphodiester backbone of the nucleic acid to the substrate would, thus, seem to be the best way of attachment for these purposes.

Binnig and Rohrer, the inventors of STM, were the first to image DNA molecules, G. Binnig et al., 49 Phys. Rev. Lett. 57–60; G. Binnig & H. Rohrer in *Trends in Physics* at 38–46, J. Janta & J. Pantoflicek, eds. (European Physical Society, The Hague, 1984), however progress has gone only as far as resolving the major and minor grooves of uncoated DNA, T. Beebe et al., 243 Science 370–72 (1989); G. Lee et al., 244 Science 475–77 (1989), and distinguishing purines from pyrimidines in uncoated polynucleotides, D. Dunlap and C.

Bustamante, 342 Nature 204–06 (1989). These experiments were conducted with highly oriented pyrolytic graphite (HOPG) substrates. HOPG was originally the obvious substrate of choice because of its advantages of having limited reactivity, low surface roughness (less than 5 Å vertical deviation over hundreds of Å lateral distance), reproducibility of flatness, low cost, and ease of preparation. However, many ambiguous HOPG surface structures could be confused with deposited biomolecules, C. Clemmer & T. Beebe, 251 Science 640 (1991), thus making HOPG an undesirable surface for this work. Thus, other substrates were sought.

Prior to 1983, gold had not been extensively investigated as a substrate for chemisorption studies due to its relative inertness towards molecular oxygen, and even carbon monoxide interacted only weakly. Nuzzo and Allara, 105 J. Am. Chem. Soc. 4481–83 (1983), discovered that thiols and disulfides could be adsorbed from solution to form ordered monolayers on gold films. The monolayers are formed because of relatively strong (30–40 kcal/mole) covalent bonds between the sulfur and gold molecules.

Bain et al., 111 J. Am. Chem. Soc. 321 (1989), and Bain et al., 111 J. Am. Chem. Soc. 7155 (1989), described further the nature of the bonds formed between organosulfur compounds and gold. The following information is extracted from these two articles. There is a specific interaction of gold with sulfur and other "soft" nucleophiles and a low reactivity toward most "hard" acids and bases. The strong specific interaction between gold and sulfur atoms in thiols, disulfides, and certain other sulfur-containing compounds induces spontaneous assembly of an adsorbed monolayer at the gold-solution interface. It is the formation of strong, coordinative gold-sulfur bonds that drives the spontaneous assembly of these monolayers. It is the position of Bain et al. that the species ultimately formed on the gold surface by adsorption of thiols from solution is a thiolate (Au-SR). It is stated, however, that the mechanism by which an initially physisorbed thiol is converted to a chemisorbed thiolate remains unclear. In other words, while the mechanics of the chemistry are not clear, the fact that bonds are formed is known. Monolayers of alkanethiols on gold appear to be stable indefinitely in air or in contact with liquid water or ethanol at room temperature.

Concerning the kinetics of formation of monolayers, Bain et al., 111 *J. Am. Chem. Soc.* 321, 328 (1989), stated that the rate of formation of a self-assembled monolayer is influenced by many factors, some of which can be controlled relatively easily, such as temperature, solvent, concentration and chain length of the adsorbate, and cleanliness of the substrate. Other factors, such as the rate of reaction with the surface and the reversibility of adsorption of the components of the monolayer, are inherent to the system. They concluded that experimental conditions must be established for each new system studied. At moderate concentrations (ca. 1 mM), the adsorption process is characterized by two distinct phases, an initial period of rapid adsorption lasting a few minutes in which the monolayer reaches a thickness of 80–90% of its maximum, and a slower period lasting several hours, during which the thickness slowly approaches its final value. This behavior can be rationalized by rapid adsorption of an imperfect monolayer followed by a slower process of additional adsorption and consolidation, possibly involving displacement of contaminants, expulsion of included solvent from the monolayer, and lateral diffusion on the surface to reduce defects and enhancing packing.

This discovery led to work involving a wide range of applications in fields including electrochemistry, biology, and microlithography. Related chemical systems have been utilized for STM of DNA molecules. In L. Bottomley et al., 10 J. Vac. Sci. & Tech. 591 (1992), a gold surface was activated by reaction with N,N-dimethyl-2-mercaptoethylamine to create a monolayer of exposed cationic groups. DNA was then bound to the monolayer by coulostatic interactions. This result offered one possible resolution to the major problem of holding nucleic acids in place during STM and AFM imaging.

U.S. Pat. No. 5,106,729 to Lindsay et al. describes a method of attaching base-substituted, phosphate-substituted, or sugar-substituted polynucleotides to gold substrates for analysis by STM or AFM. In this method, oxygen atoms in the base, phosphate, or sugar of the polynucleotide are replaced by sulfur atoms. The sulfur-containing polynucleotide is then treated with a mercury compound or other metal-containing compound to form complexes between the mercury or other metal and the sulfur atoms for enhancing contrast during the imaging process. Then, the metal-complexed polynucleotide is attached to the gold substrate by Faradaic deposition (electrodeposition) by holding the gold substrate about 1–2 V positive with respect to a reference electrode. It is believed that the mercury forms an amalgam with the gold substrate, thus binding the polynucleotide to the substrate. Subsequent imaging is performed in water. This method does not ensure that covalent bonds are formed directly between the nucleic acid and the substrate to firmly attach the nucleic acid to the substrate nor that the bases are exposed and unreacted so that they can be imaged or otherwise analyzed.

Herein is described a method of using gold-thiol monolayer chemistry to anchor nucleic acids for imaging by STM and AFM. Instead of activating the gold substrate for binding of the nucleic acids by coulostatic interactions, or binding the nucleic acids to the gold substrate by forming an amalgam between a nucleic acid-metal complex and the gold substrate, the nucleic acids are activated to permit covalent bonding of the phosphate backbone of the nucleic acid to the gold substrate, thus leaving the bases exposed and unreacted for imaging and analysis. In view of the foregoing discussion, it will be appreciated that these advantages are a significant advancement in the art.

OBJECTS AND SUMMARY OF THE INVENTION

It is an object of the present invention to provide a method of anchoring nucleic acids to a surface to permit structural analysis of the nucleic acid by scanning tunneling microscopy, atomic force microscopy, Auger electron spectroscopy, and the like.

It is another object of the invention to provide a method of attaching nucleic acids to a surface so that the DNA does not move during the structural analysis.

It is also an object of the invention to provide a method of attaching nucleic acids to a surface so that attachment is through the phosphodiester backbone.

It is another object of the invention to provide a method of attaching nucleic acids to a surface so that the nitrogenous bases are exposed for structural analysis.

It is a further object of the invention to provide a method of attaching nucleic acids to a surface so that the nitrogenous bases may be analyzed by scanning tunneling microscopy and atomic force microscopy.

It is still another object of the invention to provide a method of attaching nucleic acids to a surface for analysis by Auger electron spectroscopy.

It is yet another object of the invention to provide a method of attaching nucleic acids to a surface that is atomically flat and free of artifacts that interfere with scanning tunneling microscopy and atomic force microscopy.

It is yet a further object of the invention to provide a method of attaching nucleic acids to a gold surface.

A still further object of the present invention is to provide a method and means of anchoring thiolated DNA or RNA to a gold surface to permit the sequencing of nucleotides in the DNA or RNA chain by scanning tunneling microscopy, atomic force microscopy, Auger electron spectroscopy, and the like.

These and other objects may be accomplished by a method for adsorbing nucleic acids to the surface of a gold substrate for analyzing the structure of the nucleic acid that includes the steps of thiolating the nucleic acid by substituting at least one non-bridging internucleotide oxygen of each phosphodiester moiety with sulfur, depositing the thiolated nucleic acid on the gold surface, and subjecting the nucleic acid to analysis by means for determining the atomic or molecular structure thereof. The gold surface is prepared by subjecting a gold single crystal to mechanical polishing, electropolishing, cleaning by cycles of $Ar^+$ sputtering and annealing under vacuum until no contamination is detected by Auger electron spectroscopy, and flame annealing and quenching in methanol. A gold surface can also be prepared by vapor deposition on an atomically flat surface such as mica. The thiolated DNA is deposited on the gold surface for a sufficient time for covalent bonds to form between the sulfur and the gold. Scanning tunneling microscopy, atomic force microscopy, and Auger electron spectroscopy are used to analyze the nucleic acid structure. As used herein the terms DNA and RNA can be used interchangeably because the invention is applicable to the thiolation and attachment to gold surfaces of both molecules. By "thiolation" is meant the substituting of at least one non-bridging internucleotide oxygen of each phosphodiester moiety in the nucleotide chain with sulfur for the subsequent formation of an Au—S—P covalent bond and not the formation of thiol or mercapto ("—SH") groups on the nucleotide bases.

DETAILED DESCRIPTION

Scanning Tunneling Microscopy

Figure 1:
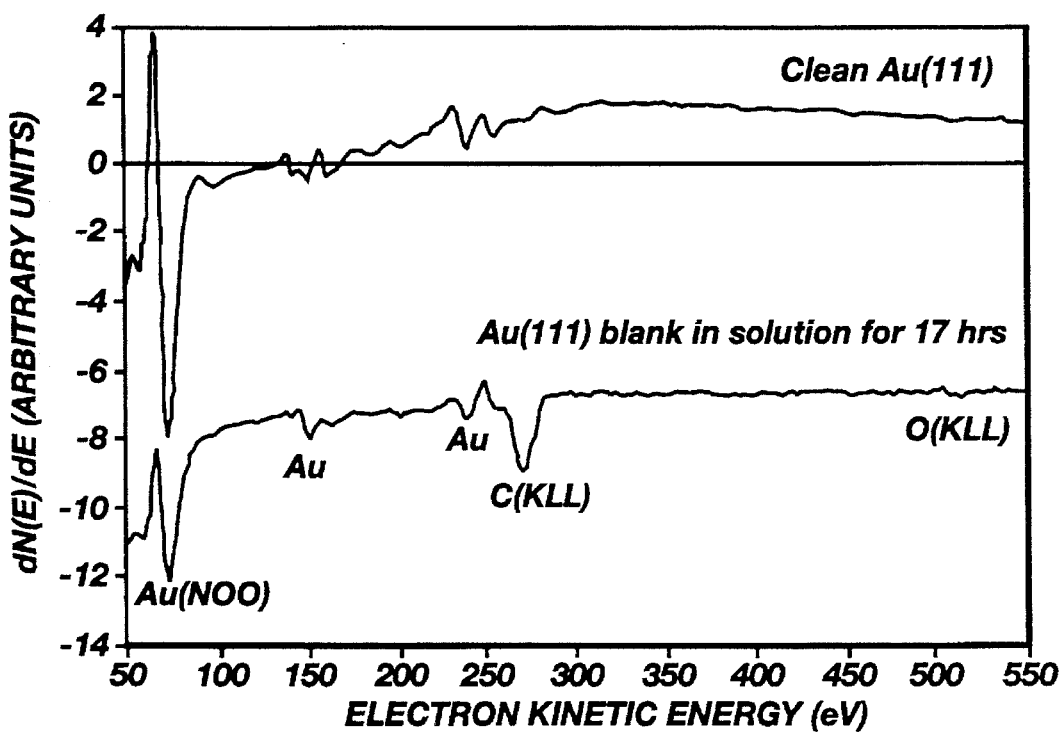
FIG. 1 is a graph of results from Auger electron spectroscopy of a clean gold single crystal and a gold single crystal which had been treated with water for 17 hours.

The scanning tunneling microscope used in this work was a coaxial double-tube piezo design built at the University of Utah. A similar design has been described in J. Lyding et al., 152 J. Microscopy 871–78 (1988), and D. Zeglinski et al., 61 Rev. Sci. Inst. 8769–74 (1990), which are hereby incorporated by reference. The microscope consists of an outer piezoelectric tube responsible for sample x, y, z offset and macroscopic initial sample approach, and an inner piezoelectric tube responsible for the x, y, z scanning of the STM tip. The tips were made of a platinum/rhodium (10% rhodium) alloy wire (0.51 mm diameter), and were prepared by either ac etching or mechanical cutting. All tips were subjected to quality control experiments. Only tips capable of obtaining atomic resolution in preliminary experiments on a freshly cleaved HOPG surface were used.

STM images were obtained at room temperature in air at varying tip scan speeds. A tunneling current set point of less than 1 nA was used. A differential input preamplifier, in which a "noise" input is electronically subtracted from a "signal plus noise" input, was incorporated into the setup. The "noise" input is connected to a wire which makes a path that is nearly identical to the path made by the "signal plus noise" wire leading to the tip. This "noise" wire terminates near the STM tip without making electrical contact. This preamplifier operates with a gain of 0.10 nA/V on a ten volt full scale with a unity gain bandwidth of approximately 2 kHz and a noise level of approximately 2 pA peak-to-peak. The STM was controlled using feedback, scanning, and offset electronics built at the University of Utah, and images were acquired using an 80386/387 based 20 MHz AT compatible computer system equipped with a 12-bit, 150 kHz analog-to-digital converter. Images consist of 256×256 arrays of 12-bit data obtained in the constant current imaging mode. Image figures were photographed from the computer screen.

Auger Electron Spectroscopy

Auger electron spectroscopy (AES) analyses were performed in an ultrahigh vacuum (UHV) surface science chamber designed and built at the University of Utah. The standard surface analysis equipment was obtained from Leybold-Heraeus as bolt-on components, which were attached to the custom designed UHV chamber. The UHV chamber has a base pressure of less than $5.0 \times 10^{-11}$ Torr which is achieved with a combination of ion, titanium sublimation, and turbomolecular pumps. A sample transfer interlock facilitates the transfer of samples in and out of ultrahigh vacuum in approximately ten minutes with only a momentary rise of the base pressure. The sample temperature can be varied from 77 K to 1500 K while being monitored with a chromel/alumel thermocouple attached to the sample. The instrumentation and data collections are controlled using data acquisition and graphics computer programs.

The typical chamber pressure for this work was less than $1 \times 10^{-9}$ Torr, and the plane of the sample was analyzed normal to the entrance axis of the hemispherical kinetic energy analyzer with the electron gun positioned at a 60 degree angle with respect to the surface normal and working distances of approximately 25 mm. The AES spectra were obtained in the derivative mode at a primary beam energy of 3000 eV and 5 V peak-to-peak modulation of the pass energy.

Preparation of Biological Samples

A pentadecanucleotide (15-mer) with a sulfur group bonded to every phosphorus atom in the phosphodiester backbone was obtained from Amersham (Arlington Heights, Ill.). The generalized structure of any nucleotide of this 15-mer, including the location of the sulfur group, is:

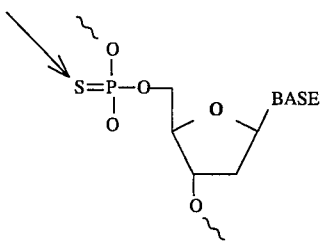

For comparative purposes, an octanucleotide (8-mer) containing one thiolated guanine moiety was prepared according to the method of M. Christopherson & A. Broom, 19 Nucl. Acids Res. 5719–24 (1991). The structure of this thiolated guanine is:

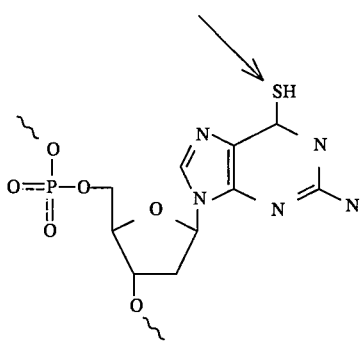

Also, for comparative purposes, brominated poly(dA) was obtained commercially. The structure of brominated adenylate is:

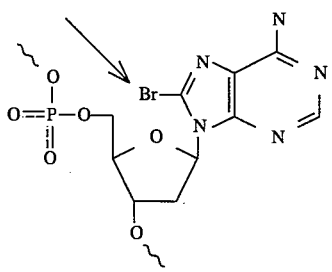

Oligonucleotides or polynucleotides having the desired modifications, in which non-bridging internucleotide oxygen atoms are replaced with sulfur, may be prepared in several ways. These methods would be obvious to one of ordinary skill in the art. Illustrative of these methods is solution-phase synthesis and solid-phase synthesis by automated DNA synthesizers. Hydrogen-phosphonate, phosphorothioamidite, and phosphoramidite chemistries may be selected. Detailed procedures for the phosphoramidite, phosphorthioamidite, and hydrogen-phosphonate methods of oligonucleotide synthesis are described in the following references, which are incorporated by reference: Caruthers et al., U.S. Pat. Nos. 4,458,066 and 4,500,707; Koester et al., U.S. Pat. No. 4,725,677; Matteucci et al., 103 J. Amer. Chem. Soc. 3185–91 (1981); Caruthers et al., 4 Genetic Engineering 1–17 (1981); Jones, chapter 2, and Atkinson et al., chapter 3, in Gait, ed., Oligonucleotide Synthesis: A Practical Approach (IRL Press, Washington, D.C., 1984); Froehler et al., 27 Tetrahedron Letters 469–72 (1986); Garegg et al., 27 Tetrahedron Letters 4051–54 and 4055–58 (1986); Andrus et al., U.S. Pat. No. 4,816,571; Brill et al., 111 J. Amer. Chem. Soc. 2321 (1989); and Froehler et al., 14 Nucleic Acids Res. 5399–5407 (1986).

Methods of producing sulfurized oligonucleotide analogs from products of the synthetic schemes are described in the following references, which are incorporated by reference: Stec et al., U.S. Pat. No. 5,151,510; Vu and Hirshbein, 31 Tetrahedron Letters 3005–08 (1991); Marugg et al., 12 Nucleic Acids Res. 9095–9110 (1984); Andrus et al., 8 Nucleosides & Nucleotides 967–68 (1989); Froehler, 27 Tetrahedron Letters 5575–78 (1986); and Stein et al., 188 Analytical Biochemistry 11–16 (1990).

Synthesis of sulfurized oligonucleotide analogs by enzymatic methods is also contemplated. For example, the Klenow fragment of *Escherichia coli* DNA polymerase I and the reverse transcriptase of avian myeloblastosis virus will incorporate 5'-α-thio-triphosphates into DNA by enzyme-catalyzed in vitro DNA synthesis. The following reference describes such synthesis and is incorporated by reference: Atrazhev et al., 13 Bioorg. Khim. 1045–52 (1987).

Preparation of Gold Single Crystals with Low Miller Indices

Crystals were cut from 0.25 inch diameter gold rods obtained from Metal Research, England. Rods of Au(111), Au(110), and Au(100), respectively, were used. The crystals were oriented using a Laue camera. Then the crystals were mechanically polished with successively smaller alumina or diamond grit, ending with 0.05 micron polishing grit, according to standard metal single crystal polishing procedures. Following mechanical polishing, the crystals were electropolished according to the method described in W. Peck & S. Nakahara, 11 Metallurgy 347–54 (1978), which is hereby incorporated by reference. The crystals were then cleaned in the UHV chamber by cycles of $Ar^+$ sputtering (500 eV, 75 minutes) and annealing (500 degrees C.) until no contamination could be detected by AES. The Au(111) surface was then flame annealed with a Bunsen burner and quenched in methanol. Caution must be exercised at this step because the methanol usually ignites and burns with a nearly invisible flame. Properly prepared gold films with the appropriate cleanliness and flatness can also be employed.

Adsorption to Gold Crystals

The samples of oligo- and poly-nucleotides in aqueous solution were deposited on gold crystals by three methods. In the preferred method, at least 15 μl of sample solution containing 3 to 10 μg/mL of oligo- or poly-nucleotide was pipetted onto a clean 5 mm diameter Au(111) single crystal and left for at least 10 hours. To prevent evaporation of the solution on the crystal during this extended time, the crystal was enclosed in a covered Petri dish containing a small amount of water to saturate the atmosphere. Following incubation, the gold crystal was washed three times with distilled ("Nanopure") water and then the crystal was allowed to air dry. The second method involved pipetting 15 μl of sample solution onto the surface of a 5 mm Au(111)

single crystal and then incubating for about 5 minutes. Then, the remaining liquid was removed by blotting with filter paper and the crystal was washed three times in distilled water and permitted to air dry. The third method consisted of pipetting 15 μl of sample solution onto a 5 mm diameter Au(111) single crystal and permitting the liquid to evaporate to dryness in air.

Results of AES on Clean, Blank, and DNA Deposited Gold Crystals

Nuzzo and Allara, 105 J. Am. Chem. Soc. 4481–83 (1983), discovered that the soft acid/soft base interactions of sulfur and gold result in monolayers of thiols and disulfides on surfaces of gold films. The present invention uses this sulfur/gold chemistry to covalently bond thiolated DNA to a gold surface, such as the surface of a gold single crystal.

Referring to FIG. 1, there is shown the results of AES analysis on a clean gold single crystal, in the upper trace, and a gold single crystal that had been exposed to distilled ("Nanopure") water for 17 hours, in the lower trace. The spectra are from the range of 50–550 eV and were signal averaged 50 times. The lower spectrum was displaced by -5 on the y-axis for clearer display. The crystal that was exposed to distilled ("Nanopure") water for 17 hours exhibits additional intensity of the C (272 eV, KLL) peak and the O (504 eV, KLL) peak compared to the clean crystal. No nitrogen, sulfur, phosphorus, or bromine peaks were observed. The following AES signals could be used to measure DNA adsorption: nitrogen (379 eV, KLL), sulfur (152 eV, LMM), phosphorus (120 eV, LMM), and bromine (1396 eV, LLM). Carbon and oxygen signals which exceed the levels found in the blank (gold single crystal exposed to distilled ("Nanopure") water for 17 hours) would also indicate DNA deposition.

Figure 2:
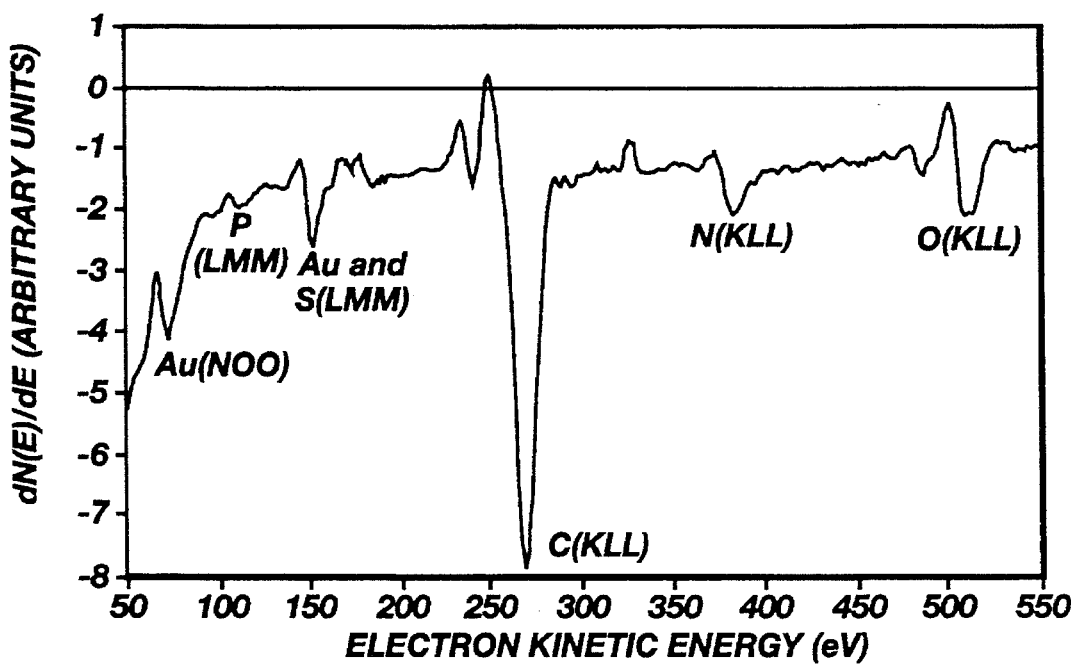
FIG. 2 is a graph of results from Auger electron spectroscopy of a gold surface on which a pentadecanucleotide (15-mer) containing a thiolated backbone was deposited.

FIG. 2 shows an AES spectrum obtained with the 15-mer containing a thiolated phosphodiester backbone that was deposited on the gold single crystal by interaction of the gold crystal and the sample solution for more than 12 hours. The spectrum was signal averaged 50 times. The spectrum contains a significant nitrogen (379 eV, KLL) peak and, thus, illustrates a positive verification of nucleic acid deposition on the gold crystal. Because of the overlap between the sulfur (152 eV, LMM) signal and the gold (150 eV, NO0) signal and the complete absence of a bromine (1396 eV, LMM) signal, the nitrogen (379 eV, KLL) signal was the most straightforward for detecting adsorption of DNA to the gold crystal.

DNA adsorption to the gold crystal might be detected by means of the sulfur (152 eV, LMM) signal if the spectral overlap of the sulfur (152 eV, LMM) peak with a secondary gold (150 eV) peak could be accounted for. A method to accomplish this goal was developed. A clean gold crystal in UHV exhibits a gold (150 eV) peak intensity that is 3% of the gold (69 eV) peak intensity. This contribution of the gold (150 eV) peak to the combined gold (150 eV) +sulfur (152 eV) peak was removed according the equation:

$$I_{152eV}^{S} \propto I_{152eV}^{S+Au} - (0.03 \cdot I_{69eV}^{Au})$$

Figure 3:
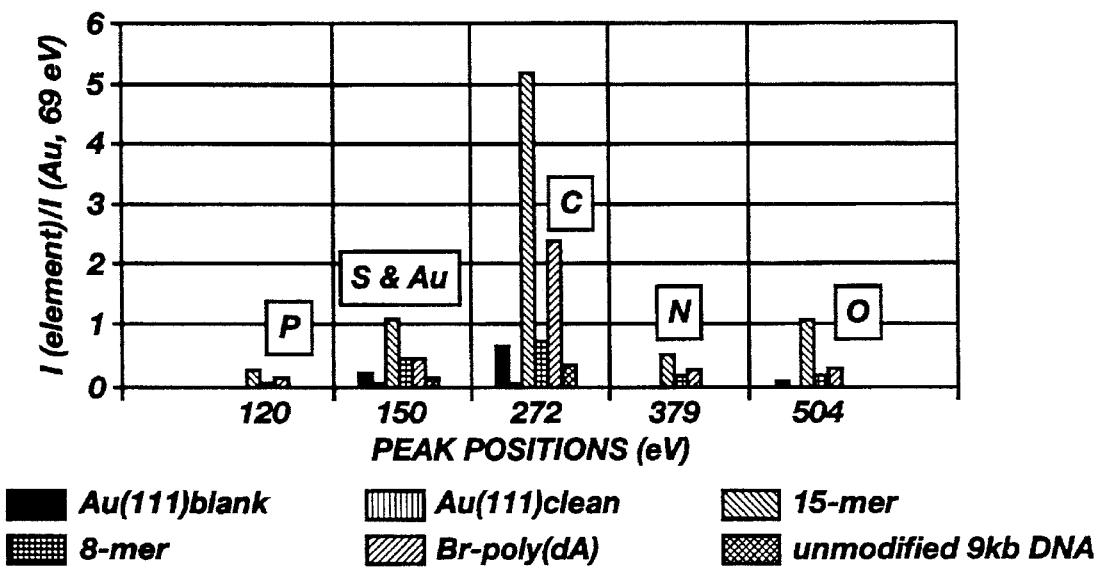
FIG. 3 is a graph showing peak ratios characteristic of DNA deposition and ratioed with respect to the principal gold peak for modified and unmodified DNA samples compared to clean and blank gold samples.

The resulting quantity was expressed as a ratio against the gold (69 eV) peak intensity to yield the results shown in FIG. 3. These results illustrate that the DNA containing a thiolated backbone adsorbed to a greater extent than the other forms of DNA tested: the 8-mer containing a thiolated guanine, brominated poly(dA), and an unmodified 9 kilobasepair plasmid double-stranded DNA.

It is known that the intensity of the gold (69 eV, NOO) peak is sensitive to sample position, thus the secondary gold (240 eV) peak has been used as a measure of the gold signal, D. Jaffey & R. Madix, 258 Surf. Sci. 359 (1991). However, carbon also exhibits an AES peak in the 240 eV range. The contribution of carbon to the AES spectrum obtained when DNA is bound to a gold single crystal can be removed in a manner similar to that just described for removing the contribution of the gold (150 eV) peak. The carbon signal at 240 eV in the absence of gold is 8.1% of the primary carbon signal at 272 eV. This contribution can be removed from the observed intensity at 240 eV, leaving the intensity due to gold, according to the following equation:

$$I_{240eV}^{Au} \propto I_{240eV}^{Au+C} - (0.081 \cdot I_{272eV}^{C})$$

Figure 4:
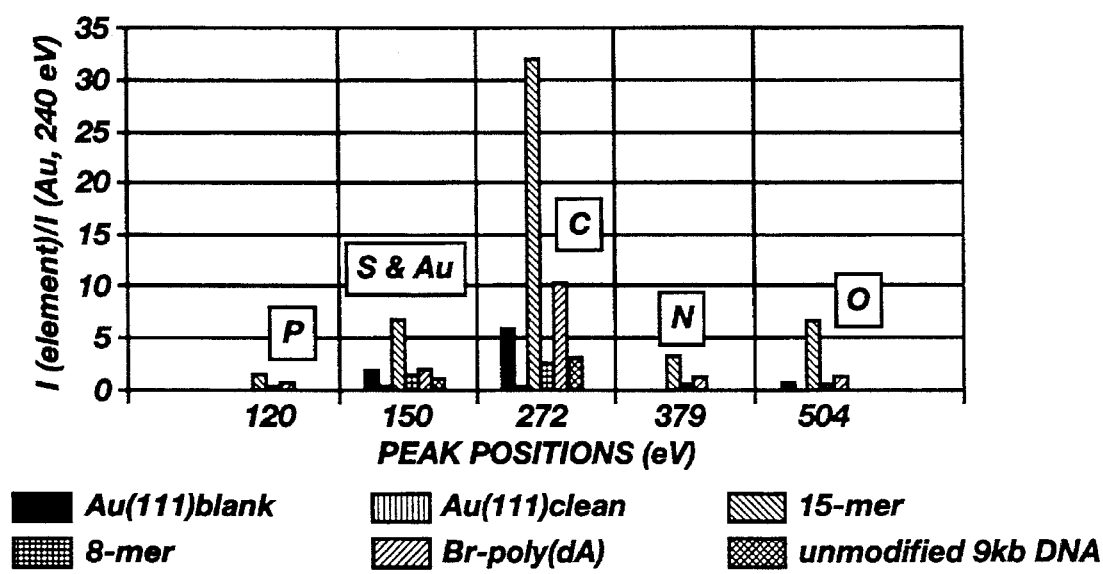
FIG. 4 is a graph showing peak ratios characteristic of DNA deposition and ratioed with respect to a secondary gold peak for modified and unmodified DNA samples compared to clean and blank gold samples.

The results of this correction, shown in FIG. 4, are analogous to those of FIG. 3 except that peak intensity ratios were calculated relative to the gold signal at 240 eV as corrected.

The AES spectrum (not shown) obtained from analysis of deposition of the brominated poly(dA) exhibited a carbon signal significantly above the background level, however the intensities of phosphorus, nitrogen, and oxygen peaks remained low. Thus, binding of brominated DNA appears less extensive than that of DNA thiolated in the phosphodiester backbone. The AES spectrum (not shown) obtained from analysis of the 8-mer containing a thiolated guanine exhibited a sulfur signal slightly above background levels, but the carbon, nitrogen, and oxygen signals were indistinguishable from background. This result suggests that little, if any, DNA containing a single thiol group adsorbed to the gold substrate. The AES spectrum obtained with an unmodified 9 kilobasepair double-stranded DNA suggested no binding at all to the gold single crystal. These results indicate that, among the modifications studied, backbone sulfur modifications are the key to successful binding of DNA to Au(111).

The adsorption of DNA to gold single crystals by placing the DNA solution on the crystal and withdrawing the liquid with a filter paper was also examined with AES. Occasionally a small nitrogen peak could be detected when the 15-mer with thiolated backbone and brominated poly(dA) were tested. However, peaks indicative of DNA adsorption were never detected with the 8-mer containing thiolated guanine. Thus, an extended period of time is required for the reaction between the thiol group and the Au(111) surface.

The adsorption of DNA to the gold surface by completely evaporating the liquid from the sample was also examined by AES. The 8-mer containing thiolated guanine was the only DNA used in this example. Characteristic DNA peaks were readily discernible (not shown). However, calculations based on the concentration of the sample, size of the DNA molecule, size of the crystal, and ideal packing conditions indicate that the DNA was deposited in a film about 100 monolayers thick on the average. The nature of this sample is not suitable for STM and AFM imaging because most of the molecules are not directly attached to the surface, thus motion and conductivity problems are expected.

Angle-Dependent X-ray Photoelectron Spectroscopy of Sulfur-Modified DNA on Au(111)

Angle-dependent x-ray photoelectron spectroscopy (ADXPS) was used to investigate the role of sulfur in the binding of a 7250-base backbone-sulfur-modified DNA on a Au(111) film on mica. Even though the presence of sulfur facilitated adsorption of DNA, as shown above, the issue of whether the sulfur was directly bound to the Au(111) surface was not answered.

The technique of ADXPS is well-suited for non-destructive quantitative depth profiling of adsorbates on surfaces. Nefedov, 17 Surf. Interface Anal. 825 (1991); Baschenko et al., 53 Electron Spectrosc. 1 (1990); Andrade, 1 Surface and Interfacial Aspects of Biomedical Polymers 140 (J. Andrade ed., 1985); Paynter et al., 2 Surface and Interfacial Aspects of Biomedical Polymers 189 (J. Andrade ed., 1985); Tillman et al., 6 Langmuir 1512 (1990); Bain et al., 111 J. Am. Chem. Soc. 321 (1989); Holloway et al., 18 Surf. Interface Anal. 251 (1992). The technique relies on the known attenuation of photoelectron intensities as a function of depth when emitted from within a sample. By changing the take-off angle of the sample with respect to the detector, the relative depths of the elements of the adsorbate can be obtained. ADXPS has been used for relative depth profiling of organic molecules and biomolecules adsorbed onto surfaces. Andrade, 1 Surface and Interfacial Aspects of Biomedical Polymers 140 (J. Andrade ed., 1985); Paynter et al., 2 Surface and Interfacial Aspects of Biomedical Polymers 189 (J. Andrade ed., 1985). ADXPS has been applied to self-assembled monolayers of alkanethiols adsorbed onto gold. Tillman et al., 6 Langmuir 1512 (1990). The atomic composition of a monolayer of $HS-(CH_2)_{10}-CO_2CH_3$ on gold was derived from ADXPS and the results suggested the monolayer structure was comprised of ester groups at the surface of the layer and sulfur on the substrate. Bain et al., 111 J. Am. Chem. Soc. 321 (1989). The results should be regarded as semi-quantitative, since many assumptions must be made about the adlayer structure and the nature of the photoelectron ejected from a solid, indicating primarily the relative positions of the elements of the adsorbate deposited on a surface.

The ADXPS technique has been extended to the reconstruction of quantitative depth profiles of multielement surfaces. Nefedov, 17 Surf. Interface Anal. 825 (1991); Baschenko et al, 53 Electron; Spectrosc. 1 (1990); Holloway et al., 18 Surf. Interface Anal. 251 (1992); Tyler et al., 14 Surf. Interface Anal. 443 (1989). These methods are variations of tomographic reconstruction methods, and allow estimates of elemental concentrations as a function of depth. In general, this reconstruction cannot obtain unique solutions with finite samples of data, and every method must address this difficulty. The method applied herein adapts the method of Nefedov, 17 Surf. Interface Anal. 825 (1991), and Baschenko et al, 53 Electron Spectrosc. 1 (1990), but is extended to include a more general form of depth profile, to be performed more quickly, and to be consistent in form with the initial data.

This study of the chemically modified DNA deposited onto Au(111) involved the use of a polynucleotide strand (7250 bases) with a sulfur-modified backbone at each phosphate position (hereinafter, S-DNA). S-DNA was prepared by an in vitro polymerase reaction using single-stranded M13 DNA as the template and α-thio-nucleoside triphosphates as precursors for synthesis of the sulfur-labeled complementary strand. Thus, the S-DNA was double-stranded, containing the unmodified template strand and the completely substituted thio-nucleotide strand. The concentration of the S-DNA was 10µg/mL in a dilute Tris buffer, pH 7.2. The S-DNA solution was heated to 90° C. for three minutes to denature and separate the sulfur-modified single strand from the template strand. A 100 µL droplet of S-DNA solution was then placed on the front face of a 1 cm² Au(111) surface. Surfaces were prepared by vapor deposition of 200 nm of Au onto freshly cleaved mica surfaces at $P \approx 10^{-6}$ to $10^{-7}$ Torr at a rate of 0.3 nm·s⁻¹. Following deposition, the substrates were annealed in vacuo at 500° C. for 60 minutes and then slowly cooled to room temperature. DeRose et al., 256 Surf. Sci. 102 (1991); Clemmer et al., 6 Scanning Microscopy 319 (1992). To prevent evaporation of the droplet on the gold surface during the extended time of interaction, the sample was enclosed in a covered Petri dish containing a small amount of water to saturate the atmosphere. After the interaction time had elapsed, the gold surface was rinsed with nanopure water three times and allowed to dry in air. Following the completion of the deposition, the sample was mounted onto an ultrahigh vacuum (UHV) sample holder, transferred through the interlock into UHV, and analyzed by ADXPS.

ADXPS experiments were performed in a stainless steel UHV surface science chamber with a base pressure of less than $5.0 \times 10^{-11}$ Torr, as described in Leavitt et al., 65 Rev. Sci. Instrum. pages 75–79 (1994), and hereby incorporated by reference. The surface of the sample was analyzed by ADXPS at variable take-off angles to the entrance axis of the hemispherical kinetic energy analyzer with the x-ray gun positioned at a 65° angle with respect to the hemispherical kinetic energy analyzer. The spectrometer acceptance angle was 0.025 steradian, which corresponds to a ±5° uncertainty in the take-off angle Θ (defined as the angle between the surface plane and the outgoing electron trajectory). The ADXPS spectra were collected in pulse-counting mode at a constant absolute resolution (pass energy ΔE-100eV) using an $AlK_\alpha$ source at an anode power of 240 W. Each ADXPS spectrum underwent a background subtraction collected on a blank gold surface for each angle to eliminate interference of signal from residual gas that adsorbed to the substrate before the sample was transferred into vacuum, and especially from other sample-mount interferences, both of which were generally very small. The instrumentation control and data acquisition were achieved as described in Leavitt et al., 65 Rev. Sci. Instrum. pages 75–79 (1994), and hereby incorporated by reference. Signal averaging was employed to increase the signal-to-noise ratio.

Elemental concentration depth profiles were calculated as follows. The intensity of the ADXPS line for each species i in an n-component sample may be described by $$I_i \propto F_i \sigma_i \int_0^\infty c_i(z) \exp(-z/\lambda_i \sin\theta) dz, \quad \text{(Eq. 1)}$$

where $F_i$ is the spectrometer transmission function, $\sigma_i$ the photoionization cross-section, $c_i(z)$ the concentration at depth z from the sample surface, $\lambda_i$ the photoelectron mean free pathlength, and Θ the photoelectron take-off angle with respect to the surface. In quantitative ADXPS it is typical to consider the intensity ratios with respect to one of the species to eliminate the proportionality constant of Eq. 1 and any corrections for variation in effective sample area with Θ.

Nefedov, 17 Surf. Interface Anal. 825 (1991), and Baschenko et al., 53 Electron Spectrosc. 1 (1990), have treated the sample as a flat homogeneous substrate covered by M-1 parallel homogeneous layers of thickness d, with total volume conservation throughout the sample, so that $c_i(z) = c_i(j)$ for $(j-1)d < z \leq jd$, $1 \leq j \leq M-1$ $c_i(z) = c_i(M)$ for $z > (M-1)d$ $$\sum_{i=1}^{n} v_i c_i(j) = \sum_{i=1}^{n} C_i(j) = 1, \quad 1 \leq j \leq M$$

where $v_i$ is the molar volume of element i, and $C_i(j) = v_i c_i(j)$ are the elemental volume fractions. Under these conditions their analysis has shown that for a set of K take-off angles $\Theta_k$, the ratios of line intensities $R_i(\Theta_k) = I_i(\Theta_k)/I_n(\Theta_k)$ then obey $$R_i(\theta_k) = \frac{F_i\lambda_i\sigma_i v_i}{F_n\lambda_n\sigma_n v_n} \left\{ \sum_{j=1}^{m-1} C_i(j)\exp\left(-\frac{(j-1)d}{\lambda_i\sin\theta_k}\right)\left[1-\exp\left(-\frac{d}{\lambda_i\sin\theta_k}\right)\right] + C_i(M)\exp\left(-\frac{(M-1)d}{\lambda_i\sin\theta_k}\right) \right\} + \quad \text{(Eq. 2a)}$$

$$R_1(\theta_R)\sum_{i-1}^{n}\left\{\sum_{j=1}^{M-1} C_i(j)\exp\left(-\frac{(j-1)D}{\lambda_n\sin\theta_k}\right)\left[1-\exp\left(-\frac{D}{\lambda_n\sin\theta_k}\right)\right] + C_i(M)\exp\left(-\frac{(M-1)d}{\lambda_n\sin\theta_k}\right) \right\}$$

The physical requirement of non-negative volume fractions also adds constraints on the unknowns:

$$c_i(j) \geq 0 \quad \text{for} \quad \leq i \leq n-1, \quad \sum_{i-1}^{n-1} c_i(j) \leq 1. \quad \text{(Eq. 2b)}$$

This system (Eq. 2) of linear relations in the (n-1)M unknowns $C_i(j)$ may then be solved to obtain the depth profiles of elemental concentration, $c_i(j)$.

Although Eq. 2a may be cast in the matrix form r=Qc, the constraints (Eq. 2b) prevent a simple solution by matrix inversion. Nefedov et al. have imposed the added constraint that each profile may have no more than one extremum, and have solved Eq. 2 by the method of conjugate gradients. Natterer, The Attenuated Radon Transform, in *Mathematics and Computer Science in Medical Imaging* (M. Viergever & A. Todd-Pokropek eds., 1988). Alternatively, we have used a least-squares modified sequential simplex method to solve Eq. 2; details of the modified sequential simplex method of Deming and Morgan may be found elsewhere. Deming et al., 45 Anal. Chem. 278A (1973). This iterative method is simple to implement, and easily incorporates the constraints of Eq. 2b. The present ADXPS implementation calculates the response estimator $\hat{r}$ for a trial set of profiles $\hat{c}$, as $\hat{r}=Q\hat{c}$; if $\hat{c}$ satisfies Eq. 2b, the error measure is the residual sum of squares $\epsilon^2=|r-\hat{r}|^2$, otherwise $\epsilon^2$ is set to be very large. The simplex method then seeks to minimize $\epsilon^2$. The iterations stop when the size of the simplex, relative to its distance from the origin, is less than a given tolerance. The best estimator e is then reported, which contains the concentration profiles for each element $C_i(j)$. The relation $$c_i(j) = 100\% \times \frac{C_i(j)}{v_i\left[\frac{1}{v_n} + \sum_{1}^{n-1} C_i(j)\left(\frac{1}{v_i} - \frac{1}{v_n}\right)\right]}$$

converts the volume fractions to concentrations in atomic percent.

Generally, the inversion of ADXPS data is an ill-posed problem, meaning that unique solutions cannot be obtained. To address this problem and seek physically sound results, the algorithm first calculates the apparent atomic percents at each angle and uses these, along with nearby points, as the initial depth profile guesses $\hat{c}_i$ for optimization. Then the results undergo repeated cycles of weighted binomial smoothing and simplex optimization. The averages and standard deviations of the profiles from these cycles, and their goodness of fit to the original intensity ratios via Eq. 2, were obtained for S-DNA on Au(111) and are reported in the next section.

The application of Eq. 2 requires several sets of parameters. All intensity ratios were measured with respect to gold, whose $(4f_{5/2}+4f_{7/2})$ photoelectron mean free path $\lambda$ was taken to be 19 Å. Ashley et al., 4 Surf. Interface Anal. 52 (1982). The cross sections $\sigma_i$ were calculated from Scofield, 8 Electron Spectrosc. 129 (1976), total cross-sections and tabulations, Reilman et al., 8 J. Electron Spectrosc. 389 (1976), of β (a constant characteristic of the atomic orbital and atomic number) for all AlK$_\alpha$ radiation, with a fixed instrumental angle of 65° between x-ray incidence and photoelectron detection. The $\lambda_i$ were estimated as proportional to $E_k^{0.7}$, and the spectrometer transmission function, Leybold-Heraeus Energy Analyzer EA 10/100, 4–5, $F_i$ as proportional to $E_k^{-1}$; nevertheless, all $E_k$ for this sample are sufficiently similar that these two contributions may be negligible. The molar volumes $v_i$ were estimated by mean molar volumes for the elements in their solid states. The number of layers M and layer thickness d were varied to ensure consistency of results.

Figure 6:
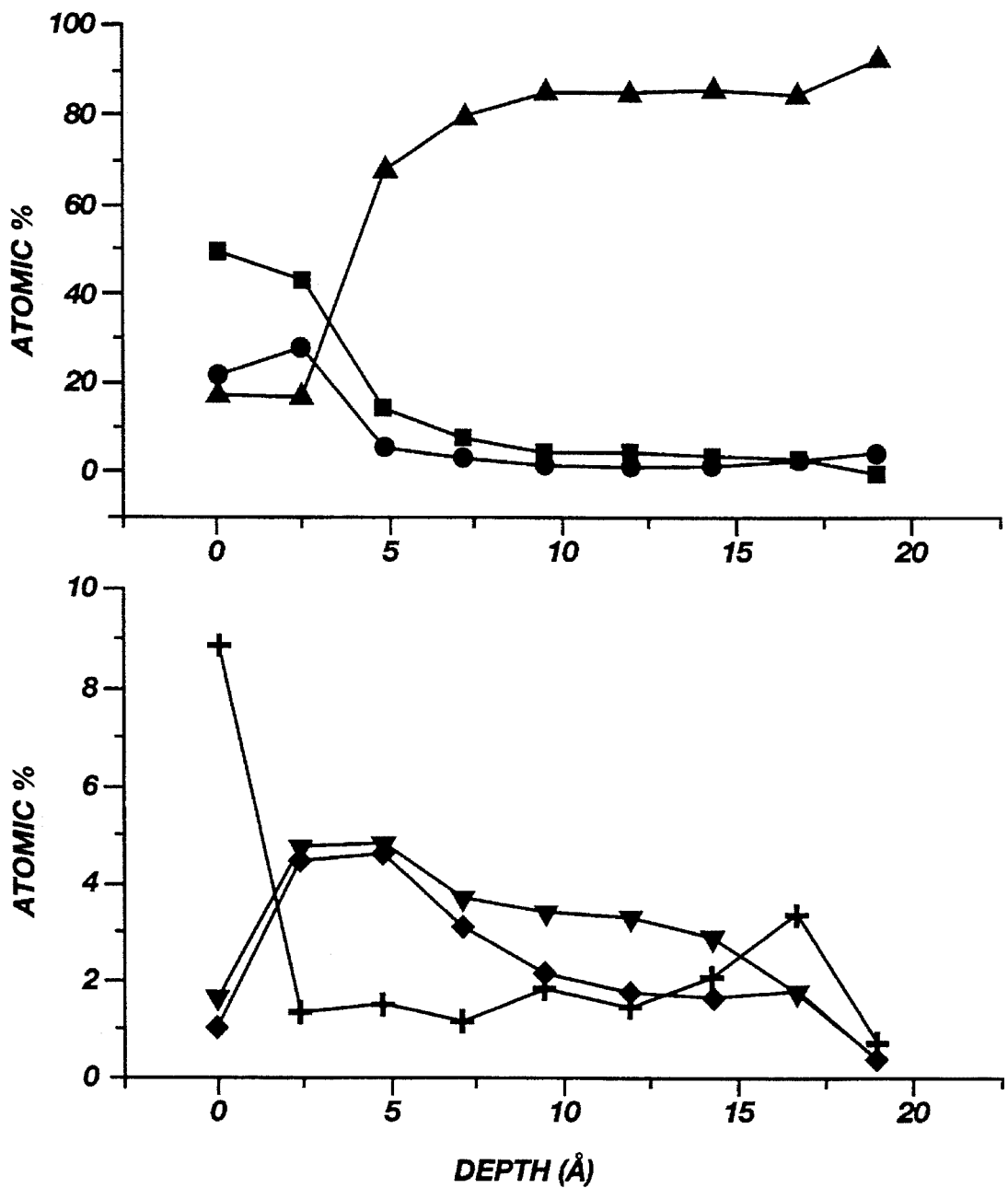
FIG. 6 shows elemental depth profiles for S-DNA on Au(111). The upper panel shows C, ■; O, ●; and Au, ▲; and the lower panel shows P, ▼; S, ♦; and N, +.

Table 1 lists the ADXPS data for S-DNA on the Au(111) surface. The ADXPS volume density for each element was calculated by $$\rho_{i,k} = \frac{I_0\sigma_{i,k}\lambda_{i,k}T_{i,k}}{N_{i,k}}$$

where $P_{i,k}$ is the volume density of atom i, $I_0$ is the x-ray flux incident on the sample, $\sigma_{i,k}$ is the differential photoionization cross section for the kth electron of atom i, $\lambda_{i,k}$ is the mean free path of the kth electron of atom i, $T_{i,k}$ is the instrument transmission function, and $N_{i,k}$ is the experimentally determined peak intensity (area) for the kth shell of atom i. FIG. 6 shows the atomic volume density of each element plotted against take-off angle $\Theta$. All intensity ratios were measured with respect to gold.

TABLE 1

| ADXPS Volume Density Ratios for S-DNA Deposited onto Au(111) | | | | | |
|---|---|---|---|---|---|
| $\Theta$ | P(2p)/Au(4f) | S(2p)/Au(4f) | C(1s)/Au(4f) | N(1s)/Au(4f) | O(1s)/Au(4f) |
| 5 | 0.0430 | 0.0549 | 1.0915 | 0.3455 | 0.5698 |
| 10 | 0.0325 | 0.0465 | 0.8988 | 0.1688 | 0.4338 |
| 20 | 0.0128 | 0.0290 | 0.5340 | 0.0536 | 0.2556 |
| 40 | 0.0055 | 0.0137 | 0.2786 | 0.0298 | 0.0758 |
| 60 | 0.0039 | 0.0060 | 0.1785 | 0.0270 | 0.1029 |
| 80 | 0.0029 | 0.0174 | 0.1457 | 0.0304 | 0.1114 |
| 85 | 0.0037 | 0.0052 | 0.1186 | 0.0305 | 0.0902 |
| 90 | 0.0017 | 0.0063 | 0.1121 | 0.0371 | 0.0983 |

Figure 5:
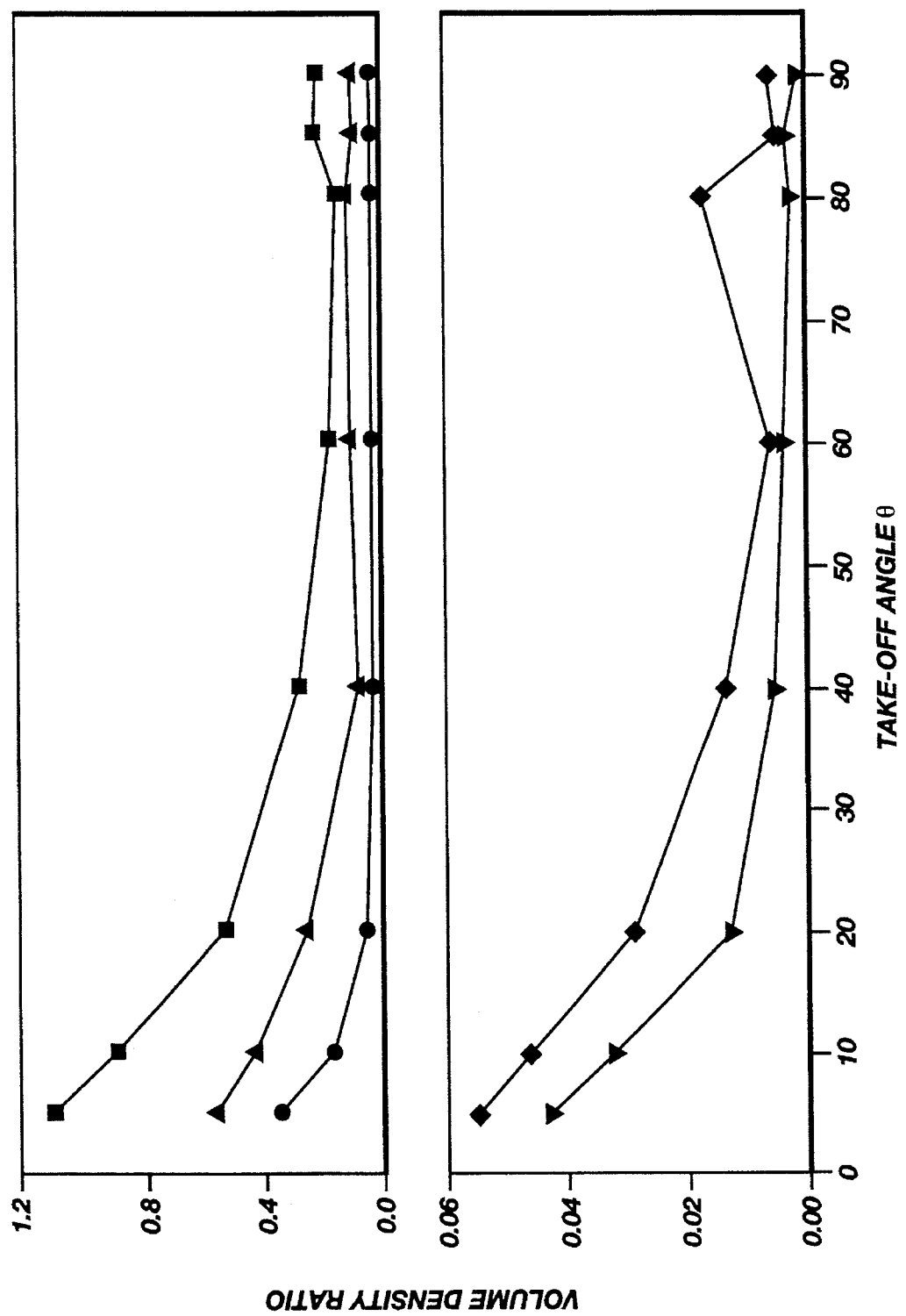
FIG. 5 shows volume density ratios of the elements with respect to Au(4f) that comprises the S-DNA plotted versus take-off angle. The upper panel shows N(1s)/Au(4f), ●; O(1s)/Au(4f), ▲; C(1s)/Au(4f), ■; and the lower panel shows P(2p)/Au(4f), ▼; and S(2p)/Au(4f), ♦.

As the take-off angle was decreased from the highest angle of 90° to the lowest angle of 5° as shown in FIG. 5, the experiment became more surface sensitive. The trend for carbon shows it at its highest ratio at the surface of the adlayer, then the ratio falls as the profile extends deeper into the surface (take-off angle was increased). All of the other elements that comprise the S-DNA followed the same trend as carbon, with the notable exception of sulfur. The ratio of sulfur was highest at the surface of the adsorbate, then fell with increasing take-off angle. A reproducible local maximum occurred at the 80° take-off angle in which the sulfur volume density ratio was approximately 3 times the volume density ratios of the take-off angles at 60° and 85°.

Further analysis of the ADXPS intensity ratio data produced quantitative depth profiles according to the method described above. The simplex-optimized fitting of the unknowns to Equation 2 with convergence tolerance set at 0.1%, implemented on an IBM-compatible 486-33 MHz computer, could perform about 33 iterations per second, needing about 10–15 minutes to complete all calculations. The results shown in FIG. 6 are the depth profiles for gold, carbon, nitrogen, oxygen, phosphorus, and sulfur, where the error bars represent ±1σ limits on the mean values (hydrogen was not analyzed). The ratio of the sum of squares for error, to the total sum of squares of $R_i(\Theta_k)$ is 0.002. This nonlinear goodness-of-fit statistic is a measure of the accuracy of the results, corresponding roughly to a linear correlation coefficient of 0.998.

The depth profiles shown in FIG. 6 had three successive regions where individual profiles reached their maximum levels. The top 5 Å of the adlayer/substrate contained the maximum levels for carbon, nitrogen, and oxygen, and relatively low concentrations of gold, phosphorus, and sulfur. From 2.5 Å to 10 Å into the overlayer, the carbon, nitrogen, and oxygen concentrations fell, while phosphorus and sulfur rose to their maximum level. In the same region, gold rose steadily. At depths greater than 10 Å, the gold fraction reached its maximum level, while phosphorus and sulfur fell steadily. The profiles also show significant depth broadening, probably due to the patchy nature of the DNA adlayer. Fadley, 11 Progress in Solid State Chemistry 265 (1976). In addition, in the top 5 Å of the adlayer, the profiles give a slight indication that the overall depth for nitrogen was less than that of carbon, and that the overall depth of oxygen was between that for carbon and the depth of the phosphorus-sulfur layer. Oxygen appeared to show an intermediate behavior between that of the carbon and nitrogen trend and the sulfur and phosphorus trend. This result would be consistent with the presence of oxygen throughout the entire molecule and the orientation of S-DNA bound at its sulfur atoms to gold.

Figure 7:
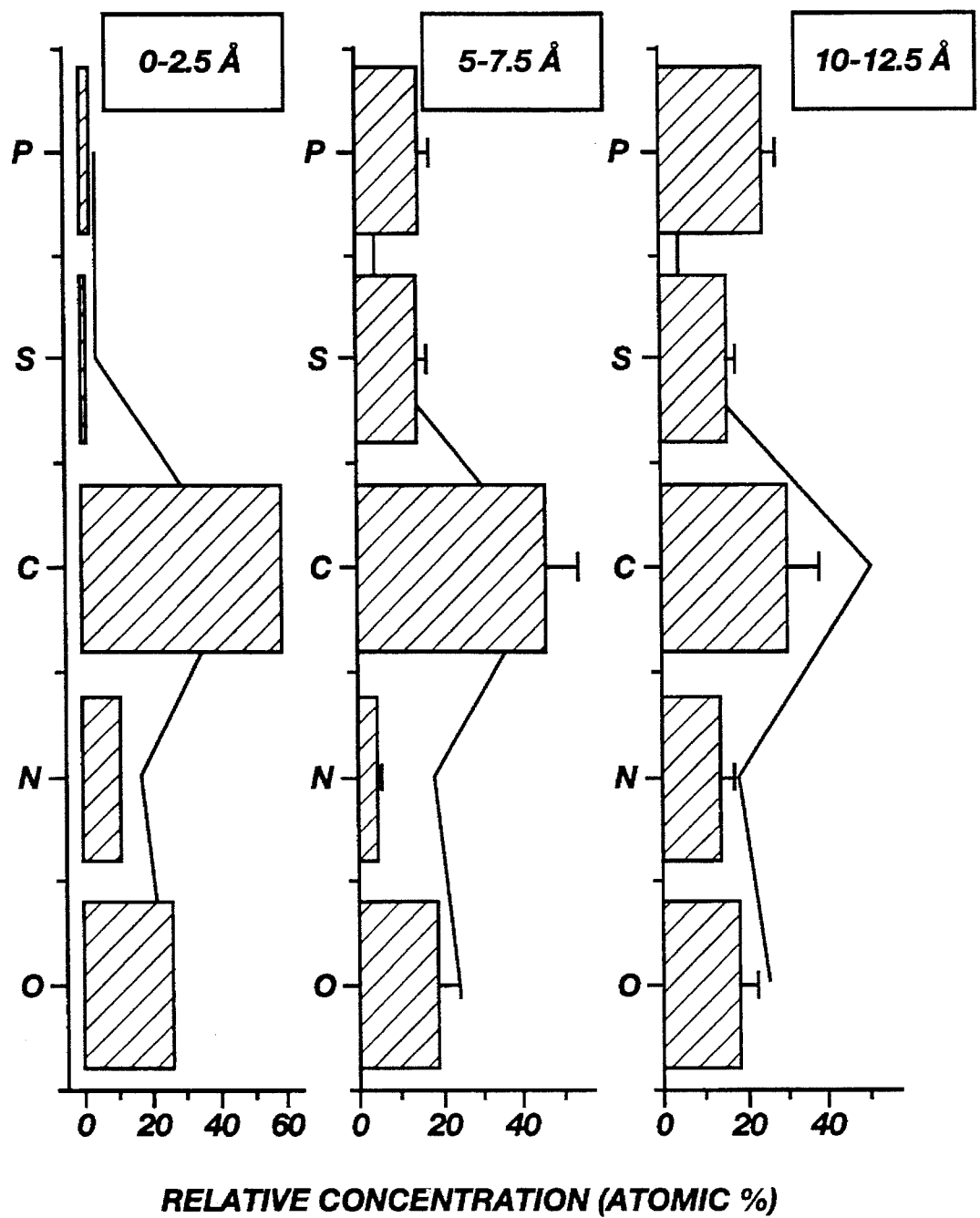
FIG. 7 shows a comparison of elemental composition for the adlayer (bars) and S-DNA theoretical mean values for the bulk DNA (line) as a function of depth into the surface.
Figure 8:
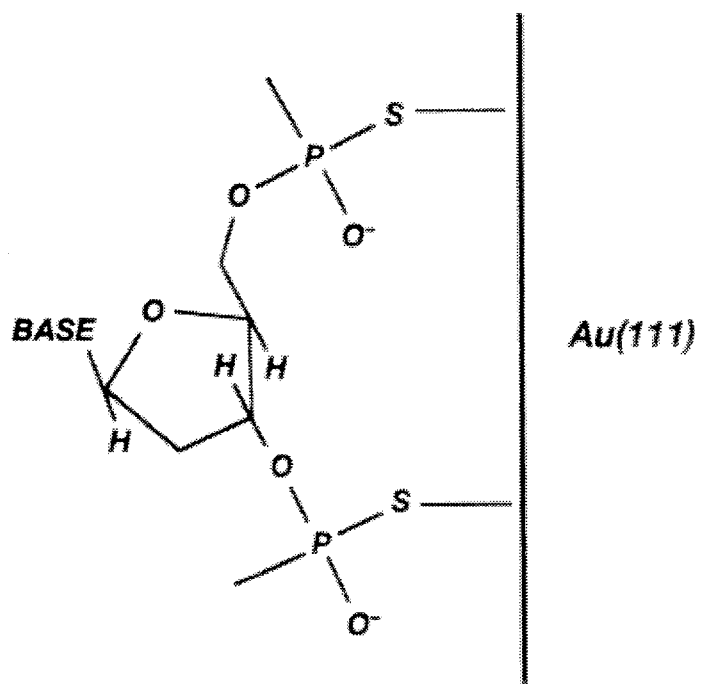
FIG. 8 shows a diagram drawn to scale of the model structure of S-DNA bound to Au(111) projected onto the depth profiles of FIG. 7.

Calculation of the relative atomic percents of carbon, nitrogen, oxygen, phosphorus, and sulfur for each region and comparison to the theoretical mean values for bulk S-DNA is shown in FIG. 7. The profiles show significant enrichment of carbon, and depletion of phosphorus and sulfur, in the top 5 Å of the adlayer. With increasing depth into the surface, phosphorus and sulfur were relatively enriched, and carbon and oxygen were depleted. The results indicate an enriched region for phosphorus and sulfur at a depth of 5–10 Å, that lies between the enriched region for carbon, nitrogen, and oxygen, and the region for gold. This agrees well with the S-DNA binding to the Au(111) surface at its backbone P=S moiety as intended by this engineered DNA modification and illustrated schematically in FIG. 8. The model structure is drawn to scale and projected onto the experimental depth profiles.

The binding model implies only that there is a significant tendency for P=S moieties to orient and bind the gold surface, not that all the moieties bind there. The unbound segments of S-DNA, if any, will tend to orient at random, so that the elements in those segments will be distributed uniformly. That uniform contribution to the elemental depth profiles will tend merely to broaden the profile features.

The possibility of artifacts caused by photoelectron diffraction and multiple scattering effects have been considered, but are not expected to be significant for the following reasons. Because of the thinness of the adlayer, only the gold substrate photoelectrons might show these effects. However, ADXPS measurements were done on Au(111) films, not on a bulk crystal. Furthermore, the fitted intensity profiles were reproduced six times in six separately prepared S-DNA/Au(111) samples, all done at randomly selected azimuthal orientations, and all producing the same experimental intensity profiles. Others have demonstrated the validity of this treatment, provided it is carried out on films as opposed to bulk crystal. Tyler et al., 7 J. Vac. Sci Technol. A 1646 (1989).

Thus, ADXPS was used to investigate the role of sulfur in the binding of backbone-sulfur-modified DNA on a Au(111) film on mica. Quantitative depth profiles for carbon, nitrogen, oxygen, phosphorus, sulfur, and gold were calculated from the ADXPS intensity ratios. An elevated concentration of sulfur, phosphorus, and oxygen between a multielement layer of the DNA molecule and the Au(111) surface was shown. These results are consistent with binding of the DNA to the Au surface at the sulfur-modified phosphate group on the backbone of the DNA.

AFM Analysis of Sulfur-Modified DNA on Au(111)

Atomic force microscopy was performed under propanol using a commercial AFM as described in Hansma et al., 20 Nucleic Acids Res. 3585 (1992), and hereby incorporated by reference, and under ambient conditions using a custom-built AFM. Silicon nitride cantilevers with force constants of 0.064 N/m and integral tips (Park Scientific, Sunnyvale, Calif.) were used for imaging. During AFM imaging, the force was reduced to the minimum (approximately 1–3 nN) needed to prevent the cantilever from lifting off of the surface. Images were acquired without filtering and subsequently underwent a least-squares background subtraction. Information density of captured images was 200×200 pixels.

Figure 9:
FIG. 9. shows a 1.2 μm×1.2 μm AFM image showing an isolated strand of sulfur-modified DNA positive contrast on Au/mica.

FIG. 9 shows a typical AFM image of S-DNA bound to the Au(111) surface, applied from a 10 μg/mL solution for 12 hours. These deposition conditions resulted in images where discernible isolated molecules were most frequently seen. Many of the images collected show that the length of the sulfur-modified DNA molecules was less than the nominal length for a 7250 bp DNA molecule. The measured lengths of the features attributed to DNA molecules ranged from 0.38 μm to 4.3 μm (n=41 images) in a bimodal size distribution. The nominal length of a stretch-out single stranded 7250-base sulfur-modified nucleotide is 2.5 to 3.9 μm. Dunlap et al., 342 Nature 204 (1989). Short molecules may have originated from incomplete synthesis of sulfur-modified complementary strands in preparation of the S-DNA. The contrast of the DNA strands was either positive, where the strands appear to be higher than the substrate, or negative, where the DNA strands appear to be lower than the substrate. As the tip starts to scan over the DNA, increased lateral and normal forces can cause a bending of the cantilever that is unrelated to topography. This bending displaces the laser beam and the z-piezo is raised to maintain the preset laser deflection, which produces a non-topographic contrast. This effect is an imaging artifact, Thundat et al., 10

J. Vac. Sci. Technol. A 630 (1992), and can operate in both the negative and positive contrast regimes, and anywhere along that contrast continuum. This artifact may also be sensitive to the scan direction relative to the cantilever geometry. The positive contrast (length=0.69 μm ±0.31 μm; n=31 images) S-DNA was typically a fifth as long as the negative contrast (length=3.1 μm ±1.2 μm; n=12 images) S-DNA. The apparent width (670±270 Å) was much larger than the nominal width of 10 Å. This overly broad apparent width is related to the curvature of the tip in combination with some possible secondary structure in the DNA. The imaging could clearly be improved by sharper tips and less destructive imaging modes.

Using AFM imaging, an average apparent coverage of the S-DNA bound to the Au(111) surface was determined as follows. The average area of the S-DNA was measured in several large-area images, and divided by the image area to yield an average apparent areal coverage of <0.01%. When the S(2p)/Au(4f) ratio averaged from all take-off angles was compared to a standard concentration curve for sulfur built up on Au(111) surface, the amount of sulfur present on the surface was about 16% of a saturated sulfur adlayer on Au(111). The low coverage measured by AFM would be undetectable by ADXPS, and suggests that scanning the probe across the surface tends to dislodge most of the weakly bound S-DNA, sweeping it out of the image area. In other images, not shown, a build-up of "debris" can clearly be seen at the edges of the image area. The comparison of the S-DNA to the S/Au(111) should only be considered as an upper limit for the concentration of S-DNA and semi-quantitative since the experimental parameters were not identical for the two cases.

The chemical shift for S(2p) has been measured after adsorption of $H_2S$ on the clean Au(111) surface and after electron irradiation to produce SH groups. The S(2p) shift for unreacted $H_2S$ on the Au(111) surface at 80 K. was 163.0±0.2 eV; for SH/Au(111) at 300 K. was 162.4±0.2 eV; for S-DNA/Au(111) at 300 K. was 161.4±0.4 eV (all shifts were calibrated for C(1s) at 285.0 eV). There was no measured chemical shift dependence on coverage for either the $H_2S$ or SH case, even though there was a large dependence of energy of desorption on coverage.

There are several possible explanations for the difference between the ADXPS and AFM measurements of apparent S-DNA coverage and for the underestimation of S-DNA length by AFM. The sulfur-gold bonds may be too weak to fully immobilize the DNA under the AFM conditions employed. It is believed that optimization of the AFM conditions will significantly reduce removal of nucleic acid by the scanning tip. Also, the AFM tip may remove DNA segments that are incompletely bound to the gold surface. Further optimization of the conditions of binding of the nucleic acid to the gold substrate will reduce the numbers of incompletely bound molecules. Contrast in scanning probe experiments of this type can be characterized along a continuum from positive to negative. The occurrence here of DNA with both positive and negative contrasts suggests the possibility of unseen segments with imperceptible contrast.

Thus, AFM studies of sulfur-modified DNA on Au(111) show that the DNA binds to the Au surface and that this binding is strong enough to immobilize nucleic acid for AFM imaging.

The above demonstrates the ability to bind or immobilize a nucleic acid to a gold substrate which is atomically flat and contaminant free, such that the nucleic acid does not move. Furthermore, it is also demonstrated that the binding of the nucleic acid to the substrate via the phosphodiester backbone of the nucleic acid takes place such that the nucleic acid is oriented for imaging of the bases. It therefore becomes apparent that structural analysis of such immobilized and oriented nucleic acids can be achieved using methods that distinguish the atomic or molecular structure of the nucleic acid. The invention therefore enables the analysis or sequencing of immobilized nucleic acids through imaging of the exposed nucleic acid bases with techniques such as scanning tunneling microscopy (STM), atomic force microscopy (AFM) and Auger electron spectroscopy. Therefore, using the present invention, the sequence of a nucleic acid can be read by visually identifying each base from an image of the nucleic acid, or by detecting some other non-visual signal (spectroscopic) which is unique to the various bases. From the above description, once the nucleotide backbone is immobilized in the manner claimed, one skilled in the art can utilize various analytical techniques to determine, analyze or sequence the bound nucleic acid. The invention, unless otherwise indicated, is therefore not limited to any particular method of thiolation of the nucleic acid, or of binding the activated nucleic acid to the gold substrate. The invention is limited only in scope by the appended claims and functional equivalents thereof.

We claim:

1. A method for immobilizing a nucleic acid, containing phosphodiester and base moieties, to a surface of a gold substrate so that the base moieties are exposed and unreacted, comprising the steps of:

(a) thiolating the nucleic acid by substituting at least one non-bridging internucleotide oxygen atom of each phosphodiester moiety in the nucleic acid with a sulfur atom; and (b) depositing the thiolated nucleic acid on the surface of the gold substrate under conditions such that a covalent bond is formed between each sulfur atom and the gold at the surface of the substrate thereby immobilizing the nucleic acid while leaving the base moieties of the nucleic acid exposed and unreacted.

2. The method as in claim 1 wherein the gold substrate comprises a gold single crystal.

3. The method as in claim 2 wherein the gold substrate comprises a single crystal of Au(111).

4. The method as in claim 2 wherein, as a preparatory step, the single gold crystal is polished and cleaned until no contamination is detected by Auger electron spectroscopy.

5. The method as in claim 4 wherein the single gold crystal is polished and cleaned by the following sequential steps:

(a) mechanical polishing;

(b) electropolishing;

(c) cleaning under vacuum by cycles of $Ar^+$ sputtering and annealing; and (d) flame annealing and quenching in methanol.

6. The method as in claim 2 wherein the nucleic acid is DNA.

7. The method as in claim 2 wherein the nucleic acid is RNA.

8. The method as in claim 1 wherein the gold substrate comprises a gold film.

9. The method as in claim 1 wherein step (b) comprises placing a solution of the thiolated nucleic acid on the surface of the gold substrate and permitting the thiolated nucleic acid solution and gold substrate to incubate together for a sufficient time for a soft acid/soft base reaction to occur between each sulfur atom and the gold such that covalent bonds are formed between each sulfur atom and the gold.

10. The method as in claim 9 wherein the thiolated nucleic acid solution and the gold substrate incubate together for a minimum of 10 hours.

11. A method for analyzing the structure of a nucleic acid, containing phosphodiester and base moieties, immobilized on the surface of a gold substrate so that the base moieties are exposed and unreacted, comprising the steps of:

(a) thiolating a nucleic acid by substituting at least one non-bridging internucleotide oxygen atom of each phosphodiester moiety of the nucleic acid with a sulfur atom;

(b) depositing the thiolated nucleic acid on the surface of the gold substrate under conditions such that a covalent bond is formed between each sulfur atom and the gold at the surface of the substrate thereby immobilizing the nucleic acid while leaving the base moieties of the nucleic acid exposed and unreacted; and (c) subjecting the immobilized nucleic acid to analysis means and determining the atomic or molecular structure thereof.

12. The method as in claim 11 wherein the analysis means of step (c) is selected from the group consisting of scanning tunneling microscopy, atomic force microscopy, angle-dependent x-ray photoelectron spectroscopy, and Auger electron spectroscopy.

13. The method as in claim 12 wherein the analysis means is scanning tunneling microscopy.

14. The method as in claim 12 wherein the analysis means is atomic force microscopy.

15. The method as in claim 12 wherein the analysis means is Auger electron spectroscopy.

16. The method as in claim 12 wherein the analysis means is angle-dependent x-ray photoelectron spectroscopy.

17. The method as in claim 12 wherein the nucleic acid is DNA.

18. The method as in claim 12 wherein the nucleic acid is RNA.

19. The method as in claim 12 wherein step (b) comprises placing a solution of the thiolated nucleic acid on the surface of the gold substrate and permitting the thiolated nucleic acid solution and gold substrate to incubate together for a sufficient time for a soft acid/soft base reaction to occur between each sulfur atom and the gold such that covalent bonds are formed between each sulfur atom and the gold.

* * * * *